United States Patent [19]
Chahwala et al.

[11] Patent Number: 6,080,761
[45] Date of Patent: Jun. 27, 2000

[54] INHIBITION OF SMOOTH MUSCLE CELL MIGRATION BY (R)-AMLODIPINE

[75] Inventors: Suresh Bababhai Chahwala; Derek Paul Winslow, both of Sandwich, United Kingdom

[73] Assignee: Pfizer Inc., New York, N.Y.

[21] Appl. No.: 08/596,365

[22] PCT Filed: Aug. 10, 1994

[86] PCT No.: PCT/EP94/02697

§ 371 Date: Feb. 21, 1996

§ 102(e) Date: Feb. 21, 1996

[87] PCT Pub. No.: WO95/05822

PCT Pub. Date: Mar. 2, 1995

[30] Foreign Application Priority Data

Aug. 26, 1993 [GB] United Kingdom .................... 9317773

[51] Int. Cl.[7] .................................................. H01N 43/40
[52] U.S. Cl. ............................................................ 514/330
[58] Field of Search .................................... 514/350, 359, 514/355, 330

[56] References Cited

U.S. PATENT DOCUMENTS 5,750,707   5/1998   Spargo ..................................... 546/321

OTHER PUBLICATIONS

Nayler, W. et al., J. Cardiovasc. Pharmacol., 17, 4, pp. 587–592 (1991).

Lakitsch, M. et al., Mol. Pharmacol., 43, 2, pp. 293–301 (1993).

*Primary Examiner*—Theodore J. Criares
*Attorney, Agent, or Firm*—Peter C. Richardson; Gregg C. Benson; James T. Jones

[57] ABSTRACT

The R(+) isomer of amlodipine is a potent inhibitor of smooth muscle cell migration despite its lack of calcium channel-blocking activity. It is useful for treating atherosclerosis, re-stenosis after angioplasty and endometriosis.

5 Claims, No Drawings

INHIBITION OF SMOOTH MUSCLE CELL MIGRATION BY (R)-AMLODIPINE

This is a National Stage filing under 35 USC §371 based on International Application PCT/EP94/02697 which was filed internationally on Aug. 10, 1994.

This invention relates to treatment of medical conditions involving smooth muscle cell migration using the R(+) isomer of 3-ethyl-5-methyl-2-(2-aminoethoxy-methyl)-4-(2-chlorophenyl)-1,4-dihydro-6-methylpyridine-3,5-dicarboxylate, a compound having the approved nonproprietary name "amlodipine".

Amlodipine is a known calcium channel-blocking agent having vasodilatory activity and is currently used, generally in the form of a pharmaceutically acceptable salt such as its maleate or besylate, in treatment of hypertension and angina. The compound and its preparation are described in European patent 0089167 B1. Amlodipine is a racemic compound due to its symmetry at position 4 of the dihydropyridine ring and the R- and S-enantiomers may be prepared by methods described in J. Med. Chem. 1986 29 1696 (Arrowsmith et al.) and European Patent Application 0331315 A. It was formerly believed that the two resolved enantiomers consisted of the R-(-) and S-(+) isomers but it has subsequently been found that these are in fact the S(-) and the R(+) isomer, respectively (see J. Med. Chem., 35, 3341–3344 (1992), Goldmann et al.). It is known that the calcium channel blocking activity of amlodipine is substantially confined to the S(-) form and the racemic mixture of R(+) and S(-) forms; the R(+) isomer has little or no calcium channel blocking activity and so is not likely to have significant cardiovascular effects when administered to a patient.

It is known that calcium channel blockers in general tend to inhibit smooth muscle cell migration. Thus they have been found to impede lesion development in various animal models of atherosclerosis (see Arteriosclerosis 5; 250 (1985), Willis et al., Arteriosclerosis 6; 237 (1986), Sugano et al.); also smooth muscle cell proliferative lesions following endothelial cell damage by balloon angioplasty are reduced by Isradipine, a calcium channel blocker (see Am. J. Pathol 124, 88–93 (1986) Handley et al.). During rest-enosis following balloon angioplasty and atherogenesis, vascular smooth muscle cells migrate from the media to the intima where they proliferate. It is believed that the efficacy of calcium channel blockers in animal models of re-stenosis post-balloon angioplasty and atherosclerosis is due to inhibition of vascular smooth muscle cell migration and subsequent reduction in smooth muscle cell proliferation and neointimal formation.

Thus, calcium channel blockers would be expected to be useful in the treatment of conditions of smooth muscle cell migration, including atherosclerosis, re-stenosis after angioplasty and endometriosis.

It has now been discovered, surprisingly and contrary to all existing theory, that the R(+) isomer of amlodipine, despite its lack of calcium channel-blocking activity, is a potent inhibitor of smooth muscle cell migration and its potency in this respect is greater that of the S(-) isomer of amlodipine and some other known calcium channel-blockers. The R(+) isomer thus provides a means of treating conditions involving smooth muscle cell migration without any concomitant cardiovascular effects.

It is therefore applicable to patients for whom reduction of blood pressure would be undesirable.

Thus, one aspect of the invention comprises the R(+) isomer of amlodipine or a pharmaceutically acceptable salt thereof for use in the treatment of conditions requiring inhibition of vascular smooth muscle cell migration.

The invention also provides use of the R(+) isomer of amlodipine or a pharmaceutically acceptable salt thereof for making a medicament for treatment of conditions requiring inhibition of smooth muscle cell migration.

A further aspect of the invention provides a pharmaceutical composition comprising the R(+) isomer of amlodipine or a pharmaceutically acceptable salt thereof and a pharmaceutically acceptable carrier or diluent, said composition being substantially free of calcium channel-blocking activity.

The invention also provides a method of treating conditions requiring inhibition of smooth muscle cell migration which comprises administering to the patient an effective amount of the R(+) isomer of amlodipine or a pharmaceutically acceptable salt thereof.

The pharmaceutically acceptable salts of amlodipine include the maleate and the besylate. The conditions to be treated include atherosclerosis, incipient re-stenosis following angioplasty, and endometriosis. The R(+) isomer of amlodipine may be used in the absence of the S(-) isomer and of any other compound acting as a calcium channel-blocker.

The effect of the R(+) isomer of amlodipine on smooth muscle cell migration was demonstrated using an aortic explant assay method in which the modulation, migration and proliferation of smooth muscle cells are assessed using primary cultures of rabbit aortic smooth muscle cells as described in Atherosclerosis 86 227–237 (1191). In this method uniform pieces of intimal/medial tissue from rabbit aorta were cultured in individual wells of a well plate. Migration was induced by addition of platelet-derived growth factor to the culture. Following a lag phase of several days the smooth muscle cells migrated from the explanted tissue and proliferated.

The distance covered by the outgrowing smooth muscle cells was measured.

This assay was carried out with varying concentrations of test compound added to the culture. The compounds thus tested were the maleate salts of the racemic mixture of R(+) and S(-) amlodipine, the maleate salts of R(+) and S(-) amlodipine separately and the known calcium channel-blocking agents nitrendipine and verapamil.

The results obtained are shown in Table 1, in which the percentage inhibition of smooth muscle cell migration for concentrations of test compound of 1 nanomole and 0.1 nanomole are recorded.

The racemic, R(+) and S(-) forms of amlodipine maleate were also tested for inhibition of $K^+$-induced rat aortic contraction by the method described by Burges et al, *J. Cardiovasc Pharmacol* 9(1) 110–9; The $1C_{50}$ (50% inhibitory concentration) values in nanomoles are also recorded in Table 1 and afford a measure of calcium channel-blocking activity.

TABLE 1

| Compound | % inhibition of SMC migration from explants | | inhibition of $K^+$ induced rat aortic contraction |
|---|---|---|---|
| | 1 nM | 0.1 nM | $1C^{50}$ (nM) |
| Amlodipine (racemate) | 33 | 39 | 2 |
| Amlodipine R (+) | 39 | 36 | 1000 |
| Amlodipine S (−) | 30 | 21 | 1 |

TABLE 1-continued

| Compound | % inhibition of SMC migration from explants | | inhibition of K⁺ induced rat aortic contraction |
|---|---|---|---|
| | 1 nM | 0.1 nM | $IC_{50}$ (nM) |
| Nitrendipine | 28 | 14 | |
| Verapamil | 22 | 13 | |

It is evident from these results that the R(+) enantiomer of amlopidine is effective in inhibiting smooth muscle cell migration even though its activity as a calcium channel blocker is negligible.

For administration to man in the curative or prophylactic treatment of conditions involving smooth muscle migration, oral doses of R(+) amlodipine or its salts may be in the range of 2–10 mg daily for an average adult patient (weighing 70 kg), that is a range similar to that used for amlodipine in the treatment of hypertension. However, the absence of cardiovascular effects allows administration of much larger doses than would be recommended for the calcium channel-blocking S(−) isomer or the racemate, with a correspondingly greater effect on cell migration. The oral dose of R(+) amlodipine or a salt thereof for the average adult patient may thus be 20 mg or more and up to 100 mg/day, or even greater. The actual dose used will be determined by a physician considering the age, weight, condition and medical history of the patient. For a typical adult patient individual tablets or capsules are likely to contain 1 to 100 mg of active compound, in a suitable pharmaceutical vehicle or carrier. Dosages for intravenous administration would be in the range of 1–20 mg of active compound per single dose as required. Thus, according to another aspect of the invention, there is provided a unit dose of a pharmaceutical composition substantially free of calcium channel-blocking activity containing (for oral administration) from 1 mg to 100 mg, preferably 20 to 100 mg, of the R(+) isomer of amlodipine or a pharmaceutically acceptable salt thereof. A further aspect of the invention provides such a unit dose for intravenous administration containing from 1 to 20 mg of the R(+) isomer of amlodipine or salt thereof.

We claim:

1. A method of treating conditions requiring inhibition of smooth muscle cell migration which comprises administering to the patient an effective amount of the R(+) isomer of amlodipine or a pharmaceutically acceptable salt thereof.

2. A pharmaceutical composition comprising the R(+) isomer of amlodipine or a pharmaceutically acceptable salt thereof and a pharmaceutically acceptable carrier or diluent, said composition being substantially free of calcium channel-blocking activity.

3. A unit dose of a composition according to claim 2, for oral administration, containing from 1 mg to 100 mg of the R(+) isomer of amlodipine or a pharmaceutically acceptable salt thereof.

4. A unit dose according to claim 3, containing at least 20 mg of the R(+) isomer of amlodipine or a pharmaceutically acceptable salt thereof.

5. A unit dose of a composition according to claim 2 for intravenous administration, containing from 1 mg to 20 mg of the R(+) isomer of amlodipine or a pharmaceutically salt thereof.

* * * * *